US00PP15209P2

(12) United States Plant Patent
McNaughton

(10) Patent No.: US PP15,209 P2
(45) Date of Patent: Oct. 5, 2004

(54) ***LAVANDULA* PLANT NAMED 'LAVSTS 15'**

(50) Latin Name: *Lavandula stoechas*
Varietal Denomination: Lavsts 15

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 0 days.

(21) Appl. No.: 10/663,847

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—S B McCormich-Ewoldt

(57) ABSTRACT

A new cultivar of *Lavandula* plant named 'Lavsts 15' that is characterized by upright semi-open habit, grey-green foliage, and white sterile bracts combined with violet corollas. These traits sets it apart from all other existing varieties of *Lavandula* known to the inventor.

2 Drawing Sheets

Genus: *Lavandula.*
Species: *stoechas.*
Denomination: Lavsts 15.

BACKGROUND OF THE INVENTION

The present invention relates to a new and distinct cultivar of lavender known botanically as *Lavandula stoechas* subsp. *pedunculata* and hereinafter referred to by the cultivar name 'Lavsts 15'. The new invention is a hybrid plant that resulted from the pollination between two *Lavandula stoechas* varieties, namely *Lavandula* 'Gethsemane' and *Lavandula stoechas* subsp. *pedunculata* and was selected in Christchurch, New Zealand by the inventor in 1996. Because of its hybrid nature, the instant plant will be known as *Lavandula* 'Lavsts 15'. The female parent is *Lavandula* 'Gethsemane' (unpatented) and the male parent plant is an unidentified cultivar of *Lavandula stoechas* subsp. *pedunculata* (unpatented).

The new lavender cultivar 'Lavsts 15' is distinct and unique due to its long peduncles that terminate in bicolor spikes, combined with grey-green foliage. There are no comparison plants, known to the inventor, that resemble the instant plant. 'Lavsts 15' is distinguishable from both parent plants by the color of foliage, spike and sterile bracts.

The new invention 'Lavsts 15' was asexually propagated by the inventor in Christchurch, New Zealand in 1996 using soft to semi-hardwood cuttings. Since that time subsequent generations have been determined fixed, stable and true to type.

SUMMARY OF THE INVENTION

The following traits have been repeatedly observed and represent the distinguishing characteristics of the new *Lavandula* cultivar 'Lavsts 15'. These traits in combination distinguish 'Lavsts 15' from all other existing varieties of *Lavandula* known to the inventor. 'Lavsts 15' has not been tested under all possible conditions and phenotypic differences may be observed with variations in environmental, climatic, and cultural conditions, however, without any variance in genotype.

1. *Lavandula* 'Lavsts 15' exhibits an upright, semi-open habit.

2. The sterile bracts and corollas of *Lavandula* 'Lavsts 15' in combination exhibit the colors white and violet blue.
3. *Lavandula* 'Lavsts 15' exhibits long tomentose, pale green peduncles.
4. *Lavandula* 'Lavsts 15' exhibits grey-green foliage.
5. *Lavandula* 'Lavsts 15' exhibits 4–8 sterile bracts per flower spike.
6. *Lavandula* 'Lavsts 15' exhibits tinges of pink coloring on the sterile bracts as the flower spikes age.

BRIEF DESCRIPTION OF THE DRAWINGS

The accompanying color drawings illustrate the overall appearance of the new cultivar 'Lavsts 15', showing colors as true as it is reasonablely possible to obtain in colored reproductions of this type. Colors in the drawings may differ from the color values cited in the detailed botanical description, which accurately describes the actual colors of the new variety 'Lavsts 15'. The plants are 6-months-old and grown out-of-doors in 1-liter containers in Christchurch, New Zealand. No chemicals were used to treat the plants.

The drawing labeled as FIG. 1 shows a mass of entire plants from an above perspective.

Figure 1:
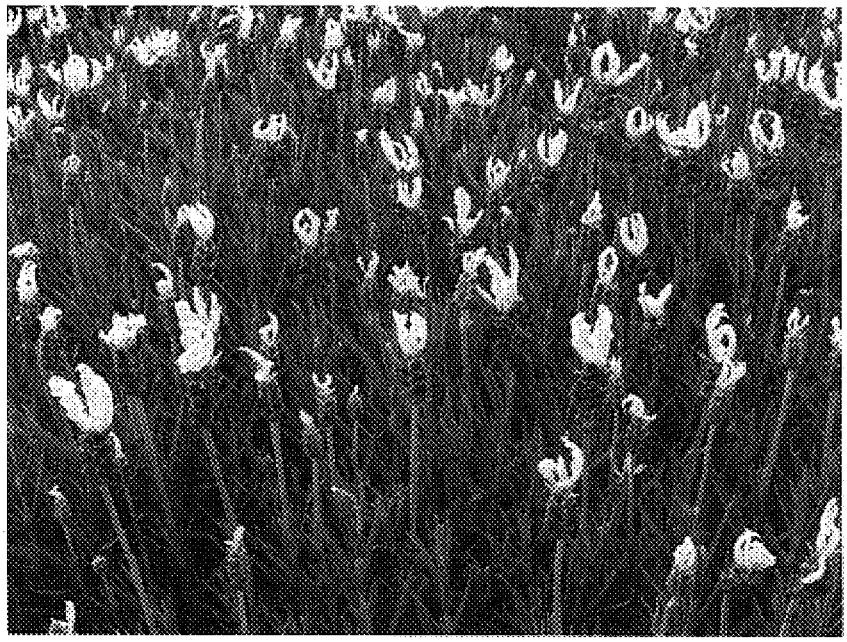
Figure 2:
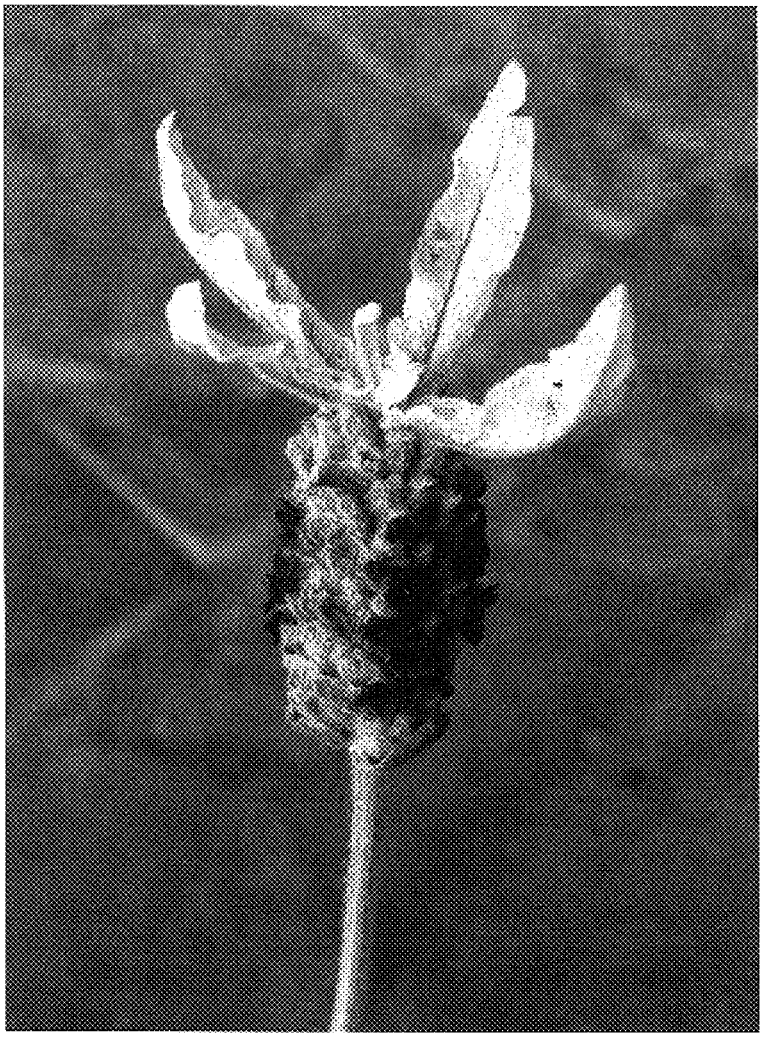

The drawing labeled as FIG. 2 shows a close-up of the flower spikes and sterile bracts.

Both drawings are made using conventional photographic techniques and although colors may appear different from actual colors due to light reflectance, they are as accurate as possible by conventional photography.

BOTANICAL DESCRIPTION OF THE PLANT

The following is a detailed description of the *Lavandula* cultivar named 'Lavsts 15'. Data was collected in West Melton, Canterbury, New Zealand from plants grown in the open ground and in dry conditions. The plants are 6-months-old and received no chemical treatments. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. Color determination using The Royal Horticultural Society Colour Chart was conducted using the light box at The New Zealand Plant Variety Rights Office at Lincoln, Canterbury, New Zealand. Please note that the brown, green and violet ranges in these charts do not have an adequate color range to match that seen in lavender. The growing requirements are similar to the species and no disease problems have been observed.

Botanical classification: *Lavandula* 'Lavsts 15'.
Species: *stoechas.*
Common name: Lavender.
Parentage: 'Lavsts 15' is a hybrid plant that is the product of pollination between the following parent plants.
*Female parent plant.*—*Lavandula* 'Gethsemane'.
*Male parent plant.*—Unidentified *Lavandula stoechas* subsp. *pedunculata.*
Type: Aromatic perennial shrub.
Use: En masse, ornamental, feature or potted plant.
Growth rate: Moderate to vigorous.
Habit: Upright and semi-open with erect, ascending flower spikes.
Disease resistance or susceptibility: No unusual or additional disease resistance or susceptibility compared to other cultivars of the species *Lavandula stoechas.*
Height: 60–70 cm in height.
Width: 60–70 cm in width.
Hardiness: USDA Zones 5–8.
Propagation method: Cuttings, tissue culture.
Root system: Fibrous.
Soil: Plant in well-drained soil.
Light levels: Plant in full sun.
Special needs: Prune after flowering to maintain shape and to initiate second flowering period.
Time to initiate roots: 21 to 36 days are needed to develop roots on an unrooted cutting.
Time to develop to a one-liter container: 3 months are needed to produce a one-Liter container from a rooted cutting.
Branching habit: Erect, upright and semi-open.
Seasonal interest: Flowers April–July and August.
Stem:
*Shape.*—Square.
*Surface.*—Densely pubescent.
*Color.*—Between dark 173D (grey-orange) and 177D (grey-orange). An exact match not possible.
*Size.*—3–5 mm in diameter.
Foliage:
*Arrangement.*—Upright stems with whorls of leaves, arranged opposite along stem. A basal pair of leaves subtend each whorl of leaves. Dense arrangement of leaves along stems.
*Leaf division.*—Simple.
*Apices.*—Acute.
*Base.*—Truncate.
*Margins.*—Entire and revolute.
*Leaf shape.*—Linear.
*Color of mature leaves* (*upper*).—138C (soft grey-green).
*Color of mature leaves* (*lower*).—138C (soft grey-green).
*Color of young leaves* (*upper*).—138A (deeper grey-green).
*Color of young leaves* (*lower surface*).—Too revolute to view.
*Upper and lower surfaces.*—Pubescent on upper surfaces, more puberulent on lower surfaces.
*Venation.*—Mid vein depressed on upper surface and protruding beneath, side veins noticeable on lower surface with magnification.
*Internodes.*—0.8–2 cm in length.
*Foliar fragrance.*—Mixture of pine and camphor.
*Petiole.*—Sessile.
*Length.*—Approximately 0.6–5 cm in length.
*Width.*—1 mm–4 mm in width.
Flower:
*Type of inflorescence.*—Terminal spike.
*Size of inflorescence.*—3–7 cm in length and 1.5–2.5 cm in width.
*Shape of inflorescence.*—Almost cylindric or fusiform-conic with sterile bracts.
*Peduncles.*—10–19 cm in height and 2–3 mm in width.
*Peduncle surface.*—Tomentose.
*Peduncle color.*—Closest to 139D (pale green but not an exact match).
*Flower shape.*—Tubular.
*Corolla.*—Two-lipped with upper lip 2-lobed and lower lip 3-lobed.
*Corolla color.*—89A (rich violet-blue but not exact match).
*Caylx color.*—Pale green but darker than peduncle colour with green appendage.
*Caylx surface.*—Pubescent.
*Bracteoles.*—None present.
*Fertile bract shape.*—Broadly obovate, rhombic-cordate and acute or suborbicular.
*Fertile bract color.*—Membranous with green veining.
*Fertile bract hair covering.*—Short hair on bracts becoming longer around the margins.
*Sterile bract shape.*—Broadly obovate, oblanceolate or linear.
*Sterile bract margins.*—Moderately undulating.
*Sterile bract length.*—15–30 mm. in length.
*Sterile bract color.*—White with green midribs. The white bracts exhibit tinges of pink as the spike ages.
*Sterile bract number.*—Four to eight in number.
*Fragrance.*—Pine.
*Blooming period* (*New Zealand*).—October to February.
*Blooming period* (*U.S.A.*).—April to August.
Reproductive organs:
*Stamens.*—4.
*Stamen length* (*2 posterior*).—2 mm.
*Stamen length* (*2 anterior*).—1 mm.
*Pistil.*—1.
*Pistil length.*—7 mm.
*Pistil diameter.*—Less than 0.25 mm.
*Filament diameter.*—Less than 0.25 mm.
*Filament color.*—Grayish-white.
*Style length.*—5 mm.
*Style color.*—Grayish-white.
*Stigma shape.*—Oval.
*Stigma color.*—Green.
*Ovary shape.*—Oblong.
*Ovary dimensions.*—Approximately 1 mm long and 0.5 mm wide.
*Ovary position.*—Superior.
*Ovary color.*—Green.
*Anther shape.*—Reniform.
*Anther length.*—0.5 mm.
*Anther color.*—Yellow-orange.
*Pollen amount.*—Sparse.
*Pollen color.*—Brown orange.

Seeds:

*Seed number.*—1–2 seeds per calyx.

*Colour of seeds.*—N200A.

*Length of seeds.*—1–3 mm. in length.

I claim:

1. A new and distinct variety of *Lavandula* plant named 'Lavsts 15' as described and illustrated.

* * * * *